(12) United States Patent
Bailey et al.

(10) Patent No.: US 7,547,752 B2
(45) Date of Patent: Jun. 16, 2009

(54) SCALP TREATMENT

(75) Inventors: Peter Lawrence Bailey, Rolling Meadows, IL (US); Helen Meldrum, Bebington (GB); Suchismita Roy, Bromborough (GB)

(73) Assignee: Unilever Home & Personal Care USA division of Conopco, Inc., Chicago, IL (US)

( * ) Notice: Subject to any disclaimer, the term of this patent is extended or adjusted under 35 U.S.C. 154(b) by 178 days.

(21) Appl. No.: 10/531,155

(22) PCT Filed: Oct. 2, 2003

(86) PCT No.: PCT/EP03/10926

§ 371 (c)(1),
(2), (4) Date: Sep. 26, 2005

(87) PCT Pub. No.: WO2004/035015

PCT Pub. Date: Apr. 29, 2004

(65) Prior Publication Data

US 2006/0104937 A1 May 18, 2006

(30) Foreign Application Priority Data

Oct. 17, 2002 (EP) .................................. 02257200

(51) Int. Cl.
*C08F 12/30* (2006.01)
*A61K 8/02* (2006.01)

(52) U.S. Cl. .................... 526/287; 514/937; 514/772.4; 526/250; 424/401; 424/70.1

(58) Field of Classification Search ................. 514/880, 514/881, 937, 724; 424/401, 70.1, 70.5, 424/59, 61; 526/287, 250
See application file for complete search history.

(56) References Cited

U.S. PATENT DOCUMENTS

| 6,011,067 A | * | 1/2000 | Hersh | .......................... 514/562 |
|---|---|---|---|---|
| 6,054,450 A | | 4/2000 | Shin et al. | .................... 514/188 |
| 6,288,115 B1 | * | 9/2001 | Bryce-Smith | ................ 514/560 |
| 6,465,421 B1 | | 10/2002 | Duranton et al. | ................ 514/1 |
| 7,067,153 B2 | | 6/2006 | Grisoni | ........................ 424/490 |
| 2003/0180277 A1 | | 9/2003 | Hoppe et al. | |
| 2003/0180278 A1 | | 9/2003 | Hoppe et al. | |
| 2004/0151682 A1 | | 8/2004 | Biehl et al. | ............... 424/70.13 |

FOREIGN PATENT DOCUMENTS

| DE | 100 36 799 | 2/2002 |
|---|---|---|
| EP | 0 116 439 A2 | 8/1984 |
| EP | 0 116 439 | 8/2004 |
| GB | 2150588 A | 7/1985 |
| WO | 00/37040 | 6/2000 |
| WO | 01/79241 A1 | 10/2001 |
| WO | 01/82861 | 11/2001 |
| WO | 02/24319 | 3/2002 |
| WO | 02/096369 | 12/2002 |

OTHER PUBLICATIONS

Kang, G. et al., "Anti dandruff shampoo composition containing climbazole and zn-pyrithione", Derwent Acc. No. 2001-481320. Feb. 5, 2001, KR 2001008904 A abstract.*
International Search Report Application No. PCT/EP 03/10926 mailed Jan. 21, 2004.
Derwent Publication XP002230172 & JP 62 192313 A assigned to Kanebo Ltd.
Notice of Opposition by Procter & Gamble, Inc. to EP 1 555 989 (Oct. 15, 2007).
Unilever reply to Opposition to EP 1 555 989 (Mar. 6, 2008).
Japanese Abstract 56-061308—published May 26, 1981.
G.A. Nowak, "*Die kosmetischen Präparate*" Band 2, 1984, pp. 489-495.
Von Horst Fey, "*Wörterbuch Der Kosmetik*", 1974, p. 219.

* cited by examiner

*Primary Examiner*—Gina C Yu
(74) *Attorney, Agent, or Firm*—Karen E. Klumas

(57) ABSTRACT

A composition for topical application to the scalp comprises (i) an anti-dandruff agent; (ii) conjugated linoleic acid; and (iii) a cosmetically acceptable diluent or carrier.

9 Claims, 1 Drawing Sheet

SCALP TREATMENT

Figure 1:
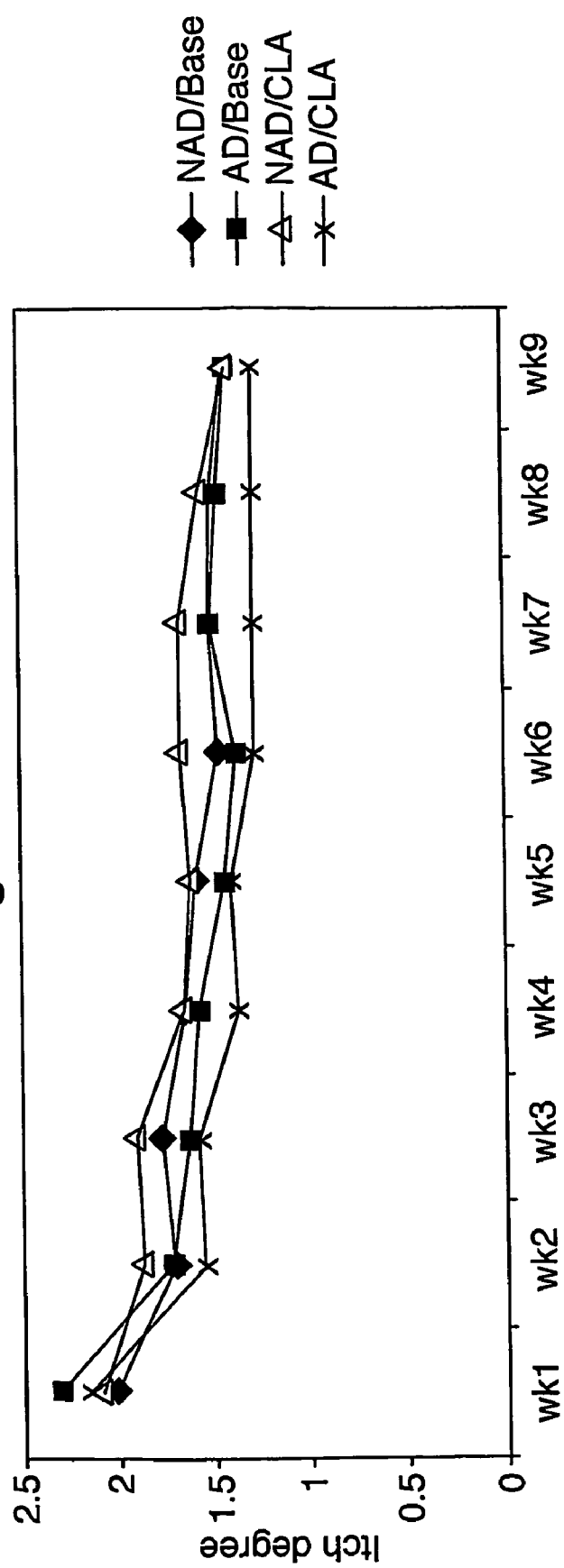

The present invention relates to compositions for topical application to the scalp, methods of treating and/or preventing dandruff and scalp itch and the use of a synergistic combination of components in the manufacture of a composition for treating and/or preventing dandruff and scalp itch.

It is widely believed that *Malassezia* yeasts, such as *Malassezia furfur*, are the main cause of dandruff. However, it is unclear why some people suffer from this condition while others do not. What is known is that increasing the level of *Malassezia* on the scalp does not automatically lead to dandruff. This suggests that *Malassezia* is necessary but not sufficient to cause the condition.

The main, if not only, intervention strategy used on the market currently for the treatment of dandruff is the topical application of antifungals such as zinc pyrithione (ZnPTO), octopirox and ketoconazole which are normally delivered from a shampoo. These antifungal agents remove (or at least reduce the level of) the *Malassezia* from the scalp, and provide effective treatment of the dandruff condition. In some cases the anti-fungal activity of these actives is complemented by the addition of a secondary active such as salicylic acid which acts as a keratolytic.

However, although clinically proven to be effective in treating the clinical symptoms of dandruff over a 2-4 week period, known anti-dandruff compositions may be less effective in treating the key consumer symptoms of dandruff rapidly and effectively. The main global consumer symptoms of dandruff are visible skin flakes in hair and on shoulders and scalp itch. Of the two symptoms, scalp itch may be the more significant symptom of dandruff.

Conjugated linoleic acid (CLA) comprises a mixture of positional and geometric isomers of octadecadienoic acid in which the two double bonds have a conjugated configuration. Natural CLA is produced by bacteria present in the rumen and can therefore be found in meat and dairy products derived from ruminants.

A number of potential health benefits have been associated with CLA. Increasing evidence exists for its effects on reducing body fat (Blankson et al. 2000, Mougios et al. 2001, Smedman et al. 2001) and its immunomodulatory effects in humans (Albers et al. 2001).

Furthermore, CLA has anti-carcinogenic and anti-inflammatory properties and reduces the risk of cardiovascular diseases. Loders Croklaan Lipid Nutrition produces CLA from safflower oil resulting in a 1:1 mixture of cis-9, trans-11 and trans-10, cis-12 isomer of CLA. This mixture is marketed in free fatty acid form (Clarinol™ A) as well as in triacylglycerol-form (Clarinol™ G).

WO 00/37040 teaches skin care compositions enriched in cis-9, trans-11 linoleic acid or derivatives thereof. The compositions are useful for the treatment and/or prevention of normal skin conditions due to ageing or chronoaging, such as wrinkles, lines, sagging, hyperpigmentation and age spots, and/or of sensitive, dry, rough, flaky, red, itchy and irritated skin.

WO 01/79241 discloses specific glycoside esters of fatty acids, such as conjugated linoleic acids, and a method for their preparation. WO 01/79241 speculates that the compounds may be useful in a broad range of possible applications including cosmetics, pharmaceuticals, food supplements and animal feeds. In particular, WO 01/79241 teaches that glycoside esters of conjugated linoleic acid may prevent fat build up.

WO 02/09664 describes cosmetic or dermatological compositions comprising combinations of bioquinones, potassium channel openers and/or 5-alpha-reductase inhibitors. The compositions are said to be useful for prolonging the anagenic phase and/or for the treatment and prophylaxis of seborrhoeic symptoms. Conjugated fatty acids may optionally be present in the compositions.

EP 0116439 discloses hair tonic compositions which include fatty acids, such as petroselinic acid, linoleic acid, linolenic acid, oleic acid and arachidonic acid for alleviating dandruff and for stimulating hair growth. There is no mention in this document of conjugated linoleic acid.

There remains a need for topical compositions which are effective for both the treatment and/or prevention of dandruff and scalp itch.

Accordingly, in a first aspect, the present invention provides a composition for topical application to the scalp comprising
 (i) an anti-dandruff agent;
 (ii) conjugated linoleic acid; and
 (iii) a cosmetically acceptable diluent or carrier.

A second aspect of the invention is a system for treating dandruff comprising: a first component comprising an anti-dandruff agent; and a second component comprising conjugated linoleic acid, wherein said first component and said second component are for topical application to the scalp and are in separate compartments within said system.

In another aspect, the present invention provides a method of treating and/or preventing dandruff which comprises applying to the scalp a composition or system of the invention.

In a further aspect, the present invention relates to the use of a synergistic combination of an anti-dandruff agent and conjugated linoleic acid in the manufacture of a composition for treating and/or preventing dandruff.

In a yet further aspect, the present invention relates to a method of treating and/or preventing scalp itch which comprises applying to the scalp a composition or system of the invention.

In a still further aspect, the present invention relates to the use of a synergistic combination of an anti-dandruff agent and conjugated linoleic acid in the manufacture of a composition for treating and/or preventing scalp itch.

Anti-dandruff agents may be used alone or as mixtures of one or more such agents. Suitable examples of anti-dandruff agents include anti-fungal agents such as the heavy metal salts of pyridinethione (pyrithione), especially zinc pyridinethione, and other antimicrobials such as selenium sulphide. The anti-dandruff agents may be soluble, partially soluble or insoluble in the compositions of the invention.

The anti-fungal agents typically display a minimum inhibitory concentration of about 50 mg/ml or less against *Malassezia*.

In a preferred embodiment of the present invention, the anti-dandruff agent is selected from metal pyrithiones, climbazole, ketoconazole and octopirox.

Preferably, the anti-dandruff agent comprises an optionally substituted imidazolyl group, more preferably an unsubstituted imidazolyl group and/or a phenyl group substituted with one or two chloro substituents. Examples of such anti-dandruff agents include ketoconazole and climbazole.

A particularly preferred antifungal agent is zinc pyrithione (ZnPTO) which, on account of its relative insolubility in aqueous systems, is generally used in hair treatment compositions as a particulate dispersion. The zinc pyrithione may be used in any particle form including, for example, crystalline forms such as platelets and needles and amorphous, regularly or irregularly shaped particles.

If zinc pyrithione is present in the composition, a suspending agent is preferably used to prevent or inhibit the settling of the particles out of the composition. The average particle diameter of the zinc pyrithione particles (ie, their maximum dimension) is typically from about 0.2 to about 50 µm, preferably from about 0.4 to about 10 µm, such as about 0.1 to about 5 µm, more preferably from 0.1 µm to 1 µm as determined, for example, using a Malvern Mastersizer (Malvern Instruments, UK).

The anti-dandruff agent is preferably present in the compositions of the invention in an amount of from about 0.01% to about 10.0% by weight, more preferably from about 0.1% to about 5.0% by weight, even more preferably from about 0.1% to about 1.0% by weight, such as from about 0.2% to about 0.8% by weight eg, about 0.5% by weight.

Conjugated linoleic acid (hereinafter referred to as CLA) is a di-unsaturated long chain (C18) fatty acid. CLA comprises a group of positional and geometric isomers of linoleic acid in which various configurations of cis and trans double bonds at positions (6, 8), (7, 9), (8, 10), (9, 11), (10, 12) or (11, 13) are possible. Thus, twenty-four different isomers of CLA exist. The compositions of the invention may comprise any of these isomers, either alone or in any combination.

In the invention the term "conjugated linoleic acid" also includes derivatives of the free acid which thus comprise conjugated linoleic acid moieties.

Preferable derivatives include those derived from substitution of the carboxyl group of the acid, such as esters (e.g. triglyceride esters, monoglyceride esters, diglyceride esters, phosphoesters), amides (e.g. ceramide derivatives), salts (e.g. alkali metal and alkali earth metal salts, ammonium salts); and/or those derived from substitution of the C18 carbon chain, such as alpha hydroxy and/or beta hydroxy derivatives. Preferably, where the derivative of CLA is an ester, it is not a glycoside.

In the case of triglyceride ester derivatives, all positional isomers of CLA substituents on the glycerol backbone are included. The triglycerides must contain at least one CLA moiety. For example, of the three esterifiable positions on the glycerol backbone, the 1 and 2 positions may be esterified with CLA and by another lipid at position 3 or as an alternative, the glycerol backbone could be esterified by CLA at the 1 and 3 positions with another lipid at position 2.

The most preferred isomers of CLA for use in the present invention are the cis 9 trans 11 (c9 t11) or trans 10 cis 12 (t10 c12) isomer. Preferably at least 1% by weight of the total CLA and/or CLA moieties present in the composition is in the form of the c9, t11 and/or t10, c12 isomer. More preferably at least 20% and most preferably at least 40%, by weight of the total CLA and/or CLA moieties present in the composition, is in the form of the c9, t11 isomer and/or t10, c12 isomer.

In a particularly preferred embodiment the conjugated linoleic acid is enriched in the c9 t11 or the t10, c12 isomer. By "enriched" it is meant that at least 50% by weight of the total CLA (and/or CLA) moieties present in the composition is in the form of the cis 9, trans 11 or the trans 10 cis 12 isomer. Preferably, at least 70%, more preferably at least 80%, and most preferably at least 90% by weight of the total CLA and/or CLA moieties present in the composition, are in the form of the c9, t11 isomer or the t10 c12 isomer.

The CLA and/or derivatives thereof comprising CLA moieties according to the present invention are commercially available as oils that are rich in conjugated linoleic acid triglyceride such as Tung oil or as dehydrated castor oil (Unichema). A mixed isomer product is available from Sigma and a c9 t11 isomer enriched CLA is available from Matreya inc.

Alternatively, CLA according to the preferred embodiments of the present invention may be prepared according to the method disclosed in WO 97/18320 whose contents are incorporated herein by reference.

Wherever the term "conjugated linoleic acid" or "CLA" is used in this specification it is to be understood that the derivatives thereof comprising CLA moieties are also included. "CLA moieties" refers to CLA fatty acyl portion(s) of a CLA derivative.

The CLA to be employed in accordance with the present invention is present in the topical composition in an effective amount. Typically, CLA is present in an amount of from 0.0001% to 20% by weight of the total composition. Preferably the amount of CLA is from 0.001% to 5%, more preferably from 0.001 to 2% and most preferably from 0.01% to 1% by weight of the total composition.

The composition according to the invention comprises a cosmetically acceptable diluent or carrier to act as a vehicle for the anti-dandruff agent and conjugated linoleic acid. The diluent or carrier may comprise materials commonly employed in hair care products such as water, liquid emollients, silicone oils, emulsifiers, solvents such as, for example, ethanol and propanol, humectants, thickeners, powders, propellants and the like.

The diluent or carrier may be present in an amount of from 0.1% to 99% by weight, more preferably from 1.0% to 98% by weight of the total composition. It is particularly preferred if the diluent or carrier is present in an amount of from 15% to 96% by weight, most preferably from 25% to 95% by weight of the total composition.

Compositions of the invention typically also comprise a perfume or fragrance.

It is particularly preferred if the composition according to the present invention is a shampoo.

Such shampoo compositions will typically contain water in an amount of from about 50% to about 98% by weight, preferably from about 60% to about 90% by weight, most preferably at least 70% by weight.

A shampoo composition of the invention will also comprise one or more cleansing surfactants that are cosmetically acceptable and suitable for topical application to the hair. Further surfactants may be present as an additional ingredient if sufficient for cleansing purposes is not provided as emulsifier for any emulsified components in the composition, e.g. emulsified silicones. It is preferred that shampoo compositions of the invention comprise at least one further surfactant (in addition to that used as emulsifying agent) to provide a cleansing benefit.

Suitable cleansing surfactants, which may be used singularly or in combination, are selected from anionic, amphoteric and zwitterionic surfactants, and mixtures thereof. The cleansing surfactant may be the same surfactant as the emulsifier, or may be different.

Examples of anionic surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic surfactants for use in shampoos of the invention include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauryl isethionate and sodium N-lauryl sarcosinate. The most preferred anionic surfactants are sodium lauryl sulphate, triethanolamine monolauryl phosphate, sodium lauryl ether sulphate 1 EO, 2EO and 3EO, ammonium lauryl sulphate and ammonium lauryl ether sulphate 1EO, 2EO and 3EO.

Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

The shampoo composition can also include co-surfactants, to help impart aesthetic, physical or cleansing properties to the composition. A preferred example is a nonionic surfactant, which can be included in an amount ranging from 0% to about 5% by weight of the total composition.

For example, representative nonionic surfactants that can be included in shampoo compositions of the invention include condensation products of aliphatic ($C_8$-$C_{18}$) primary or secondary linear or branched chain alcohols or phenols with alkylene oxides, usually ethylene oxide and generally having from 6 to 30 ethylene oxide groups.

Other representative nonionics include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

$RO$-$(G)_n$ wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies in the range of from about 1.1 to about 2. Most preferably the value of n lies in the range of from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

The total amount of surfactant (including any co-surfactant, and/or any emulsifier) in shampoo compositions of the invention is generally from 0.1 to 50% by weight, preferably from 5 to 30%, more preferably from 10% to 25% by weight of the total shampoo composition.

A cationic deposition polymer is a preferred ingredient in shampoo compositions of the invention, for enhancing conditioning performance of the shampoo. By "deposition polymer" is meant an agent which enhances deposition of one or more insoluble components from the shampoo composition onto the intended site during use, i.e. the hair and/or the scalp.

The deposition polymer may be a homopolymer or be formed from two or more types of monomers. The molecular weight of the polymer (in g/mol) will generally be between 5 000 and 10 000 000, typically at least 10 000 and preferably in the range 100 000 to about 2 000 000. The polymers will have cationic nitrogen containing groups such as quaternary ammonium or protonated amino groups, or a mixture thereof.

The cationic nitrogen-containing group will generally be present as a substituent on a fraction of the total monomer units of the deposition polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range.

Suitable cationic deposition polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1-C7 alkyl groups, more preferably C1-3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic deposition polymers can comprise mixtures of monomer units derived from amine- and/or quaternary ammonium-substituted monomer and/or compatible spacer monomers.

Suitable cationic deposition polymers include, for example:

copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g. LUVIQUAT FC 370);

copolymers of 1-vinyl-2-pyrrolidine and dimethylaminoethyl methacrylate, referred to in the industry (CTFA) as Polyquaternium-11. This material is available commercially from Gaf Corporation (Wayne, N.J., USA) under the GAFQUAT tradename (e.g., GAFQUAT 755N);

cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively;

mineral acid salts of amino-alkyl esters of homo- and copolymers of unsaturated carboxylic acids having from 3 to 5 carbon atoms, (as described in U.S. Pat. No. 4,009, 256);

cationic polyacrylamides (as described in WO95/22311).

Other cationic deposition polymers that can be used include cationic polysaccharide polymers, such as cationic cellulose derivatives, cationic starch derivatives, and cationic guar gum derivatives.

Cationic polysaccharide polymers suitable for use in compositions of the invention include those of the formula:

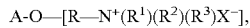

A—O—[R—N$^+$(R$^1$)(R$^2$)(R$^3$)X$^-$], wherein: A is an anhydroglucose residual group, such as a starch or cellulose anhydroglucose residual. R is an alkylene, oxyalkylene, polyoxyalkylene, or hydroxyalkylene group, or combination thereof. R$^1$, R$^2$ and R$^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in R$^1$, R$^2$ and R$^3$) is preferably about 20 or less, and X is an anionic counterion.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (Commercially available from Rhodia (formerly Rhone-Poulenc) in their JAGUAR trademark series).

Examples are JAGUAR C13S, which has a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic deposition polymer is selected from cationic cellulose and cationic guar derivatives. Particularly preferred deposition polymers are JAGUAR C13S, JAGUAR C15, JAGUAR C17 and JAGUAR C16 and JAGUAR C162.

The cationic deposition polymer will generally be present at levels of from 0.001 to 5%, preferably from about 0.01 to 1%, more preferably from about 0.02% to about 0.5% by weight of the total composition.

The compositions of the invention may comprise solid active agents. Suitable solid active agents include pigment particles, such as solid dyes or colorants suitable for application to hair, and metal colloids.

Hair treatment compositions such as shampoos and conditioners are frequently opacified or pearlised to enhance consumer appeal.

Examples of opacifying agents include higher fatty alcohols (e.g. cetyl, stearyl, arachidyl and behenyl), solid esters (e.g. cetyl palmitate, glyceryl laurate, stearamide MEA-stearate), high molecular weight fatty amides and alkanolamides and various fatty acid derivatives such as propylene glycol and polyethylene glycol esters. Inorganic materials used to opacify hair treatment compositions include magnesium aluminium silicate, zinc oxide, and titanium dioxide.

Pearlescing agents typically form thin, platelet-type crystals in the composition, which act like tiny mirrors. This gives the pearl lustre effect. Some of the opacifying agents listed above may also crystallise as pearlescing agents, depending on the media in which they are used and the conditions employed.

Typical pearlescing agents may be selected from C16-C22 fatty acids (e.g. stearic acid, myristic acid, oleic acid and behenic acid), esters of C16-C22 fatty acid with alcohols and esters of C16-C22 fatty acid incorporating such elements as alkylene glycol units. Suitable alkylene glycol units may include ethylene glycol and propylene glycol. However, higher alkylene chain length glycols may be employed. Suitable higher alkylene chain length glycols include polyethylene glycol and polypropylene glycol.

Examples are polyethylene glycol mono or diesters of C16-C22 fatty acids having from 1 to 7 ethylene oxide units, and ethylene glycol esters of C16-C22 fatty acids. Preferred esters include polyethylene glycol distearates and ethylene glycol distearates. Examples of a polyethylene glycol distearate available commercially are EUPERLAN PK900 (ex Henkel) or GENAPOL TS (ex Hoechst). An example of an ethylene glycol distearate is EUPERLAN PK3000 (ex Henkel).

Other pearlescing agents include alkanolamides of fatty acids having from 16 to 22 carbon atoms, (e.g. stearic monoethanolamide, stearic diethanolamide, stearic monoisopropanolamide and stearic monoethanolamide stearate); long chain esters of long chain fatty acids (e.g. stearyl stearate, cetyl palmitate); glyceryl esters (e.g. glyceryl distearate), long chain esters of long chain alkanolamides (e.g. stearamide DEA distearate, stearamide MEA stearate), and alkyl (C18-C22) dimethyl amine oxides (e.g. stearyl dimethyl amine oxide).

Further suitable pearlescing agents include inorganic materials such as nacreous pigments based on the natural mineral mica. An example is titanium dioxide coated mica. Particles of this material may vary in size from 2 to 150 microns in diameter. In general, smaller particles give rise to a pearly appearance, whereas particles having a larger average diameter will result in a glittery composition.

Suitable titanium dioxide coated mica particles are those sold under the trade names TIMIRON (merck) or FLAMENCO (Mearl).

The level of opacifying or pearlescing agent employed in compositions of the invention is generally from 0.01 to 20%, preferably 0.01 to 5%, more preferably from 0.02 to 2% by weight of the total composition.

Gas (e.g. air) bubbles represent another type of suspended phase that may be introduced into a hair treatment composition for aesthetic purposes. When evenly sized and homogeneously dispersed in the composition, these can enhance consumer appeal.

Compositions in accordance with the invention may also be formulated as conditioners for the treatment of hair (typically after shampooing) and subsequent rinsing.

Such a conditioner will comprise one or more conditioning surfactants which are cosmetically acceptable and suitable for topical application to the hair.

Suitable conditioning surfactants are selected from cationic surfactants, used singly or in admixture. Examples include quaternary ammonium hydroxides or salts thereof, e.g. chlorides.

Suitable cationic surfactants for use in hair conditioners of the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in hair conditioners of the invention is cetyltrimethylammonium chloride, available commercially, for example as GENAMIN CTAC, ex Hoechst Celanese.

In conditioners of the invention, the level of cationic surfactant is preferably from 0.01 to 10%, more preferably 0.05 to 5%, most preferably 0.1 to 2% by weight of the composition.

Conditioners of the invention advantageously incorporate a fatty alcohol. The combined use of fatty alcohols and cationic surfactants in conditioning compositions is believed to be especially advantageous, because this leads to the formation of a lamellar phase, in which the cationic surfactant is dispersed.

Representative fatty alcohols comprise from 8 to 22 carbon atoms, more preferably 16 to 20. Examples of suitable fatty alcohols include cetyl alcohol, stearyl alcohol and mixtures thereof. The use of these materials is also advantageous in that they contribute to the overall conditioning properties of compositions of the invention.

The level of fatty alcohol in conditioners of the invention is conveniently from 0.01 to 10%, preferably from 0.1 to 5% by weight of the composition. The weight ratio of cationic surfactant to fatty alcohol is suitably from 10:1 to 1:10, preferably from 4:1 to 1:8, optimally from 1:1 to 1:4.

The compositions of the invention may comprise one or more conditioning agents. As used herein, the term "conditioning agent" includes any material that is used to give a particular conditioning benefit to hair and/or skin. For example, in compositions for use in washing hair, such as shampoos and conditioners, suitable materials are those which deliver one or more benefits relating to shine, softness, combability, wet-handling, anti-static properties, protection against damage, body, volume, stylability and manageability.

Preferred conditioning agents for use in the present invention include emulsified silicones, used to impart for example wet and dry conditioning benefits to hair such as softness, smooth feel and ease of combability.

Various methods of making emulsions of particles of silicones for use in the invention are available and are well known and documented in the art.

The viscosity of the silicone itself (not the emulsion or the final washing composition) preferably ranges from 10,000 cps to 5 million cps. The viscosity can be measured by means of a glass capillary viscometer as set out further in Dow Corning Corporate Test Method CTM004 Jul. 20, 1970.

Suitable silicones include polydiorganosiloxanes, in particular polydimethylsiloxanes which have the CTFA designation dimethicone. An example is dimethicone fluid having a viscosity of up to 100,000 centistokes at 25° C., which is available commercially from the General Electric Company as the Viscasil series and from Dow Corning as the DC 200 series.

Aminofunctional silicones which have the CTFA designation amodimethicone, are also suitable for use in the compositions of the invention, as are polydimethyl siloxanes having hydroxyl end groups, which have the CTFA designation dimethiconol.

Also suitable are silicone gums. "Silicone gum" denotes polydiorganosiloxanes having a molecular weight of from 200,000 to 1,000,000 g/mol and specific examples include dimethicone gums, dimethiconol gums, polydimethyl siloxane/diphenyl/methylvinylsiloxane copolymers, polydimethylsiloxane/methylvinylsiloxane copolymers and mixtures thereof. Examples include those materials described in U.S. Pat. No. 4,152,416 (Spitzer), and on General Electric Silicone Rubber product Data Sheet SE 30, SE 33, SE 54 and SE 76.

Also suitable for use in the present invention are silicone gums having a slight degree of cross-linking, as are described for example in WO 96/31188. These materials can impart body, volume and stylability to hair, as well as good wet and dry conditioning.

Preferred emulsified silicones for use in compositions of the invention have an average silicone particle size in the composition of less than 100, preferably less than 30, more preferably less than 20 microns, most preferably less than 10 microns.

Particle size may be measured by means of a laser light scattering technique, using a 2600D Particle Sizer from Malvern Instruments.

Suitable silicone emulsions for use in the invention are commercially available in a pre-emulsified form. This is particularly preferred since the pre-formed emulsion can be incorporated into the washing composition by simple mixing.

Examples of suitable pre-formed emulsions include emulsions DC2-1766 and DC2-1784, available from Dow Corning. These are emulsions of dimethiconol. Cross-linked silicone gums are also available in a pre-emulsified form, which is advantageous for ease of formulation. A preferred example is the material available from Dow Corning as DC X2-1787, which is an emulsion of cross-linked dimethiconol gum.

The amount of silicone incorporated into the compositions of the invention depends on the level of conditioning desired and the material used. A preferred amount is from 0.01 to about 10% by weight of the total composition although these limits are not absolute. The lower limit is determined by the minimum level to achieve conditioning and the upper limit by the maximum level to avoid making the hair and/or skin unacceptably greasy. We have found that an amount of silicone of from 0.5 to 1.5% by weight of the total composition, is a particularly suitable level.

A further preferred class of conditioning agents are per-alk(en)yl hydrocarbon materials, used to enhance the body, volume and stylability of hair.

EP 567 326 and EP 498 119 describe suitable peralk(en)yl hydrocarbon materials for imparting stylability and enhanced body to hair. Preferred materials are polyisobutylene materials available from Presperse, Inc. under the PERMETHYL trade name.

The amount of per-alk(en)yl hydrocarbon material incorporated into the compositions of the invention depends on the level of body and volume enhancement desired and the specific material used. A preferred amount is from 0.01 to about 10% by weight of the total composition although these limits are not absolute. The lower limit is determined by the minimum level to achieve the body and volume enhancing effect and the upper limit by the maximum level to avoid making the hair unacceptably stiff. We have found that an amount of per-alk(en)yl hydrocarbon material of from 0.5 to 2% by weight of the total composition is a particularly suitable level.

When the hydrocarbon material is lipophilic, it may constitute all or part of the lipophilic agent of the invention.

Compositions useful in the present invention may also be formulated as transparent or opaque emulsions, lotions, creams, pastes or gels according to any of the methods known to the person skilled in the art.

In an alternative embodiment of the present invention, the composition is a lotion or cream for direct application to the scalp.

Compositions of this invention may contain any other ingredient normally used in hair treatment formulations. These other ingredients may include viscosity modifiers, preservatives, colouring agents, polyols such as glycerine and polypropylene glycol, chelating agents such as EDTA, antioxidants, fragrances, and sunscreens. Each of these ingredients will be present in an amount effective to accomplish its purpose. Generally these optional ingredients are included individually at a level of up to about 5% by weight of the total composition.

Preferably, compositions of this invention also contain adjuvants suitable for hair care. Generally such ingredients are included individually at a level of up to 2%, preferably up to 1%, by weight of the total composition.

Among suitable hair care adjuvants, are:

(i) natural hair root nutrients, such as amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts. A particularly preferred combination of natural hair root nutrients for inclusion in compositions of the invention is isoleucine and glucose. A particularly preferred amino acid nutrient is arginine.

(ii) hair fibre benefit agents. Examples are:
ceramides, for moisturising the fibre and maintaining cuticle integrity. Ceramides are available by extraction from natural sources, or as synthetic ceramides and pseudoceramides. A preferred ceramide is Ceramide II, ex Quest. Mixtures of ceramides may also be suitable, such as Ceramides LS, ex Laboratoires Serobiologiques. The ceramides may constitute all or part of the lipophilic agent of the invention.

Where the compositions of the invention are formulated as aqueous compositions, water is typically present in an amount of 50% to 95% by weight, more preferably from 60% to 90% by weight, more preferably from 70% to 90% by weight. Water is generally present as solvent and makes up the balance of the weight of the composition. Other solvents, such as mono- or di-hydric alcohols having from 2 to 6 carbon atoms (eg, ethanol and propylene glycol) may optionally be used as cosolvents together with water. Such cosolvents, if present, are generally present in an amount of from 0.1% to 5% by weight of the composition.

The compositions of the invention may be packaged in any suitable manner such as in a jar, a bottle, a tube, a roll-ball, or the like, in the conventional manner.

The method of the invention may be carried out from once or twice daily to once weekly to the area of the scalp that requires treatment. The improvement in the appearance and/or feel of the scalp will usually appear after one to six weeks, depending on the condition of the scalp, the concentration of the active ingredients used in the method, the amount of the composition used and the frequency with which it is applied.

In general, a quantity of the composition, for example, from 0.1 to 10 ml is applied to the scalp from a suitable container or applicator and spread over and/or rubbed into the skin using the hands or fingers or a suitable device. A rinsing step may follow depending on whether the composition is formulated as a "leave on" or a "rinse-off" product.

The system of the invention for treating dandruff (which can also be termed a kit of parts) comprises: a first component comprising an anti-dandruff agent; and a second component comprising conjugated linoleic acid (CLA). The first component and the second component are both suitable for, and are preferably adapted for, topical application to the scalp. The first component and the second component are formulated differently (for example, one component may be a lotion and the other a shampoo, or one component may be a shampoo and the other a conditioner). The first component and the second component are applied to the scalp in the desired order depending on their respective formulations (which may be formulated as described above in connection with the compositions of the invention), and the terms first and second have no significance in this regard i.e., the second component may be applied to the scalp before the first component or vice versa. The first component and the second component are in separate compartments within the system, for example the system may comprise the first and second components packaged separately and further packaged such that the system is sold as a single item or the first component and the second component may be in discrete compartments in a two-part package.

The invention will now be further illustrated by the following, non-limiting examples. In the examples and throughout the specification all percentages are by weight based on the total-weight of the composition, unless indicated otherwise.

EXAMPLES

Example 1

The following is an example of an anti-dandruff shampoo composition comprising conjugated linoleic acid in accordance with the present invention.

| Trade name | Chemical name | Level (%) 100% by wt. | Activity (%) | Level as recvd (%) |
|---|---|---|---|---|
| Conjugated Linoleic acid | Conjugated linoleic acid | 2.00 | 100.00 | 100 |
| Texapon N 70 (Henkel Shanghai) | SLES 2EO (70%) | 16.00 | 70.00 | 22.86 |
| CAPB - 30 (SH Goodway) | Coco-amido propyl betaine (30%) | 2.00 | 30.00 | 6.66 |
| Jaguar C-17 (Rhodia) | Galactomannan 2-hydroxy-propyltrimethyl-ammonium chloride ether | 0.20 | 100.00 | 0.20 |
| Zinc Omadine FPS (Yoshitomi) | Zinc pyrithione, fine | 1.00 | 48.00 | 2.08 |
| Polydimethoxy siloxane emulsion (Dow Corning) | Silicone DC1785 | 2.00 | 50.00 | 4.00 |

-continued

| Trade name | Chemical name | Level (%) 100% by wt. | Activity (%) | Level as recvd (%) |
|---|---|---|---|---|
| ETD980 (B F Goodrich) | ETD980 | 0.60 | 100.00 | 0.60 |
| Formalin (37%) (SH Solvent Factory) | Formaldehyde | 0.04 | 37.00 | 0.10 |
| Citric Acid (SH Guansheng Yuan Bio-engineer Co.) | Citric Acid | 0.10 | 100.00 | 0.10 |
| Salt (SH Salt Co.) | Sodium Chloride | 0.40 | 100.00 | 0.40 |
| Sodium Hydroxide (SH Dongfeng) | Sodium Hydroxide | 0.30 | 100.00 | 0.30 |
| Perfume, colour, minors | | | | <0.10 |
| Dem. Water | | To 100.00 | 100.00 | To 100.00 |

Example 2

Demonstrating the Anti-itch Effects of Conjugated Linoleic Acid in Combination with an Anti-dandruff Shampoo Composition A This composition is used for comparison in the following protocol.

| Trade Name | Chemical name | Supplier | Activity, % | Level as recvd, % | Level (%) 100% by wt. |
|---|---|---|---|---|---|
| Glydant plus | DMDM hydantoin, etc | Lonza | 100 | 0.2 | 0.2 |
| Tween 20 | POE(20) sorbitan mono laurate | ICI | 100 | 1 | 1 |
| Carbopol 980 | Poly acrylic acid | Goodrich | 100 | 2.5 | 2.5 |
| Sodium Hydroxide | Sodium Hydroxide | SH Dongfeng | 100 | 0.1 | 0.1 |
| Natrosol 250 HHR | Natrosol Hydroxyethyl cellulose | Aqualon | 100 | 0.3 | 0.3 |
| EDTA-2Na | Disodium Ethylene diamine tetracetic acid | Xiangde | 100 | 0.05 | 0.05 |
| Water | Water | Local | 100 | to 100% | to 100% |

Composition B includes the same components as composition A but in addition contains conjugated linoleic acid in an amount of 3.0% by weight. Composition B is also used in the following protocol.

Compositions C and D

| Trade name | Chemical name | Level (%) by 100% wt. | Activity (%) | Level as recvd (%) |
|---|---|---|---|---|
| Texapon N 70 (Henkel Shanghai) | SLES 2EO (70%) | 16.00 | 70.00 | 22.86 |
| CAPB - 30 (SH Goodway) | Coco-amido propyl betaine (30%) | 2.00 | 30.00 | 6.66 |
| Jaguar C-17 (Rhodia) | Galactomannan 2-hydroxypropyltri-methylammonium chloride ether | 0.20 | 100.00 | 0.20 |
| Zinc Omadine FPS (Yoshitomi) | Zinc pyrithione, fine | XX | | |
| Polydimethoxy siloxane emulsion (Dow Corning) | Silicone DC1785 | 2.00 | 50.00 | 4.00 |
| ETD980 (B F Goodrich) | ETD980 | 0.60 | 100.00 | 0.60 |
| Formalin (37%) (SH Solvent Factory) | Formaldehyde | 0.04 | 37.00 | 0.10 |
| Citric Acid (SH Guansheng Yuan Bio-engineer Co.) | Citric Acid | 0.10 | 100.00 | 0.10 |
| Salt (SH Salt Co.) | Sodium Chloride | 0.40 | 100.00 | 0.40 |
| Sodium Hydroxide (SH Dongfeng) | Sodium Hydroxide | 0.30 | 100.00 | 0.30 |
| Perfume, colour, minors | | | | <0.10 |
| Dem. Water | | To 100.00 | 100.00 | To 100.00 |

Composition C: XX = 0%
Composition D: XX = 1% by wt.

Composition C is a non anti-dandruff (NAD) shampoo composition used for comparison in the following protocol.

Composition D is an anti-dandruff (AD) shampoo composition used in the following protocol.

Protocol

The effect of conjugated linoleic acid, used in conjunction with anti-dandruff (AD) and non anti-dandruff (NAD) shampoo, was clinically assessed using the following protocol.

The conjugated linoleic acid is used as a lotion (composition B). The lotion base comprises Tween™ 20, Carbopol™ 980, Sodium Hydroxide, Natrosol™ 250HHR, EDTA-2Na, glydant plus and water (composition A). The use of the lotion is followed by a shampoo wash with an NAD shampoo (composition C) or an AD shampoo (composition D).

A randomised monadic double blind study design was used based on a total of 240 screened panellists, male and female, with self-perceived dandruff. All 240 panellists used a placebo shampoo (composition C) in their normal hair wash routine for 4 successive weeks.

The panellists were divided into four groups (total number of panellists=240):

Group 1: 60 panellists. All panellists wash their hair with NAD shampoo at home 3 times a week and apply CLA lotion one hour prior to washing their hair.

Group 2: 60 panellists. All panellists wash their hair with NAD shampoo at home 3 times a week and apply lotion base (composition A) one hour prior to washing their hair.

Group 3: 60 panellists. All panellists wash their hair with AD shampoo at home 3 times a week and apply CLA lotion one hour prior to washing their hair.

Group 4: 60 panellists. All panellists wash their hair with AD shampoo at home 3 times a week and apply lotion base (composition A) one hour prior to washing their hair.

After their fourth visit, the panellists are instructed not to apply lotion i.e., either base lotion (composition A), or CLA containing lotion (composition B) to their scalp prior to washing with shampoo for the remainder of the study. Panellists come to the study centre at the same frequency as before i.e., once a week for the next five successive weeks for scalp assessments and continue hair washing at home as before but without using any lotion.

In order to assess the degree of itching at each visit to the study centre, subjects are interviewed by an investigator about their itch feeling on:
1) Itch degree
2) Itch lasting time
3) Itch frequency According to the subject's response, the investigator will give a value from the standard scale for the degree of itch feeling. The standard scale is as follows:

| | |
|---|---|
| 0 = | None |
| 1 = | Mild |
| 2 = | Moderate |
| 3 = | Marked |
| 4 = | Severe |

Analysis of itch scores is carried out using analysis of variance to test for main effects and interactions of NAD and AD shampoo and CLA containing lotion. The following individual comparisons are made testing for significant differences at the 5% level. Data transforms or non-parametric methods are used where necessary.
1) Non AD shampoo+CLA lotion vs Non AD shampoo+base lotion
2) AD shampoo+CLA lotion vs AD shampoo+base lotion
3) AD shampoo+CLA lotion vs Non AD shampoo+CLA lotion The results from the above anti-itch study are summarised in FIG. 1.

FIG. 1 shows the results of the anti-itch study from the panellists in group 1 (NAD/CLA), group 2 (NAD/base), group 3 (AD/CLA) and group 4 (AD/Base) in graphical form with itch degree on the vertical axis and the week number of the protocol on the horizontal axis.

In FIG. 1, the graph shows that throughout the anti-itch study, the combination of anti-dandruff (AD) shampoo and conjugated linoleic acid lotion (CLA), as used by the panellists in group 3, unexpectedly lowers the degree of itch of the scalp compared to the compositions used in the other groups.

The results from group 3 are particularly surprising in view of the results from group 2 and group 1. Thus, the results from group 1 show that when CLA is used in combination with an NAD shampoo (NAD/CLA), the degree of itch is actually higher than when an NAD shampoo is used in combination with the base composition (composition A) as in group 2. This comparison shows that CLA can increase the degree of scalp itch.

The results from group 4 show that when an AD shampoo is combined with the base composition, the degree of itch can be lowered. When CLA is combined with an anti-dandruff shampoo, as in group 3, the degree of itch is significantly lowered. This would not have been expected from the results of group 1, which suggest that the addition of CLA should actually increase the degree of itch.

Therefore the results shown graphically in FIG. 1 indicate that there is an unexpected synergistic effect obtained from using the combination of anti-dandruff agent and conjugated linoleic acid.

The invention claimed is:

1. A composition for topical application to the scalp comprising
   (i) 0.1 to 5% by wt. of an anti-dandruff agent;
   (ii) 0.01 to 5% by wt. of conjugated linoleic acid; and
   (iii) a cosmetically acceptable diluent or carrier, wherein the anti-dandruff agent comprises zinc pyrithione.

2. A composition as claimed in claim 1, which is a shampoo.

3. A composition as claimed in claim 1, which is a lotion or cream for direct application to the scalp.

4. A composition as claimed in claim 1, wherein the anti-dandruff agent is zinc pyrithione.

5. A system for treating dandruff comprising; a first component comprising 0.1 to 5% by wt. of an anti-dandruff agent comprising zinc pyrithione; and a second component comprising 0.01 to 5% by wt. of conjugated linoleic acid, wherein said first component and said second component are for topical application to the scalp and are in separate compartments within said system.

6. A method of treating dandruff which comprises applying to the scalp a composition of claim 1.

7. A method of treating scalp itch which comprises applying to the scalp a composition of claim 1.

8. A composition according to claim 1, formulated as a transparent or opaque emulsion, lotion, cream, paste or gel, for treating scalp itch.

9. A composition according to claim 1 wherein at least 90% of the total conjugated linoleic acid present in the composition is in the form of cis 9, trans 11 and/or trans 10, cis 12 isomers.

* * * * *